(12) United States Patent
Abels et al.

(10) Patent No.: US 7,611,352 B2
(45) Date of Patent: Nov. 3, 2009

(54) LIFESTYLE BRACKET SYSTEM HAVING INTERCHANGEABLE LIGATION COVERS

(75) Inventors: Norbert Abels, Homburg (DE); Claus H. Backes, Saarbrücken (DE)

(73) Assignee: Ultradent Products, Inc., South Jordan, UT (US)

(*) Notice: Subject to any disclaimer, the term of this patent is extended or adjusted under 35 U.S.C. 154(b) by 0 days.

(21) Appl. No.: 11/469,157

(22) Filed: Aug. 31, 2006

(65) Prior Publication Data
US 2008/0057459 A1    Mar. 6, 2008

(51) Int. Cl.
*A61C 3/00* (2006.01)

(52) U.S. Cl. ............... 433/10; 433/9; 433/11; D24/180

(58) Field of Classification Search ........ 433/8–12; D24/180
See application file for complete search history.

(56) References Cited

U.S. PATENT DOCUMENTS

| | | | |
|---|---|---|---|
| 2,548,864 A | 4/1951 | Brusse ............... | 43/11 |
| 3,091,857 A | 6/1963 | Rubin et al. ........... | 43/11 |
| 3,505,736 A | 4/1970 | Brader et al. | |
| 3,969,821 A | 7/1976 | Lee, Jr. et al. | |
| 4,120,090 A | 10/1978 | Kesling | |
| 4,139,945 A | 2/1979 | DiGuilio | |
| 4,180,912 A | 1/1980 | Kesling | |
| 4,279,593 A | 7/1981 | Rohlcke | |
| 4,355,975 A | 10/1982 | Fujita | |
| 4,626,208 A | 12/1986 | Hall | |
| 4,687,441 A * | 8/1987 | Klepacki ............... | 433/8 |
| 4,712,999 A | 12/1987 | Rosenberg | |
| 4,913,653 A | 4/1990 | Bolliger et al. | |
| 4,913,654 A | 4/1990 | Morgan et al. | |
| 4,915,625 A * | 4/1990 | Tsukuma et al. ........... | 433/8 |

(Continued)

FOREIGN PATENT DOCUMENTS

DE    20314121    1/2004

(Continued)

OTHER PUBLICATIONS

Echols, Michael Dr., "How to Tighten Orthodontic Braces" from the internet URL: http://www.braceface.com/tighten.htm.

(Continued)

*Primary Examiner*—Ralph A Lewis
*Assistant Examiner*—Yogesh Patel
(74) *Attorney, Agent, or Firm*—Workman Nydegger

(57) ABSTRACT

An orthodontic bracket system including a plurality of interchangeable ligation covers so as to allow the patient and practitioner to create a desired aesthetic look. The inventive orthodontic bracket system includes a bracket base, at least one arch wire slot formed in the bracket base adapted to receive an arch wire therein, a first interchangeable ligation cover that when releasably assembled to the bracket base can be selectively moved relative to the bracket base between an open non-ligating position relative to the arch wire slot and a closed, ligating position relative to the arch wire slot, and a second interchangeable ligation cover of a different color and/or formed of a different material relative to the first cover. The interchangeable ligation covers can be removed and replaced with another cover of a different color and/or different material to create a different aesthetic appearance.

21 Claims, 14 Drawing Sheets

U.S. PATENT DOCUMENTS

| | | | | |
|---|---|---|---|---|
| 4,978,391 | A | * | 12/1990 | Jones ............................ 106/35 |
| 5,032,080 | A | | 7/1991 | Hakansson et al. |
| 5,096,417 | A | | 3/1992 | Greenberg et al. |
| 5,116,885 | A | | 5/1992 | Hattori et al. |
| 5,160,260 | A | | 11/1992 | Chang |
| 5,174,754 | A | | 12/1992 | Meritt ............................ 433/8 |
| 5,238,402 | A | | 8/1993 | Rohlcke et al. |
| 5,322,435 | A | | 6/1994 | Pletcher ........................ 433/11 |
| 5,326,259 | A | | 7/1994 | Rohlcke et al. |
| 5,429,499 | A | | 7/1995 | Sernetz ............................ 433/8 |
| 5,429,500 | A | | 7/1995 | Damon |
| 5,439,378 | A | | 8/1995 | Damon |
| 5,441,408 | A | | 8/1995 | Moschik |
| 5,542,844 | A | | 8/1996 | Perret, Jr. |
| 5,556,276 | A | | 9/1996 | Roman et al. |
| 5,607,299 | A | | 3/1997 | Nicholson |
| 5,685,711 | A | | 11/1997 | Hanson ........................ 433/11 |
| 5,692,896 | A | | 12/1997 | Pospisil et al. |
| 5,711,665 | A | | 1/1998 | Adam et al. |
| 5,711,666 | A | | 1/1998 | Hanson ........................ 433/11 |
| 5,716,208 | A | | 2/1998 | Forman |
| 5,738,513 | A | | 4/1998 | Hermann ........................ 433/13 |
| 5,762,492 | A | | 6/1998 | Kanomi |
| 5,803,728 | A | | 9/1998 | Orikasa et al. |
| 5,857,849 | A | | 1/1999 | Kurz ............................ 433/10 |
| 6,071,119 | A | | 6/2000 | Christoff et al. .............. 433/14 |
| 6,142,775 | A | | 11/2000 | Hansen et al. |
| 6,168,429 | B1 | | 1/2001 | Brown ............................ 433/11 |
| 6,220,857 | B1 | | 4/2001 | Abels ............................ 433/8 |
| 6,267,590 | B1 | | 7/2001 | Barry |
| 6,276,930 | B1 | | 8/2001 | Pozzi |
| 6,347,939 | B2 | | 2/2002 | Abels ............................ 433/10 |
| 6,350,792 | B1 | | 2/2002 | Smetana et al. |
| 6,394,798 | B1 | | 5/2002 | Huff et al. |
| 6,485,299 | B1 | | 11/2002 | Wildman ........................ 433/10 |
| 6,506,049 | B2 | | 1/2003 | Hanson |
| 6,607,383 | B2 | | 8/2003 | Abels et al. |
| 6,616,445 | B2 | | 9/2003 | Abels et al. |
| 6,655,957 | B2 | | 12/2003 | Abels et al. .................... 433/10 |
| 6,655,958 | B2 | | 12/2003 | Abels et al. .................... 433/10 |
| 6,659,766 | B2 | | 12/2003 | Abels et al. .................... 433/10 |
| 6,663,385 | B2 | | 12/2003 | Tepper |
| 6,695,612 | B2 | | 2/2004 | Abels et al. .................... 433/10 |
| 6,726,474 | B2 | | 4/2004 | Spencer ........................ 433/11 |
| 6,733,286 | B2 | | 5/2004 | Abels et al. |
| 6,960,080 | B2 | | 11/2005 | Abels |
| 6,960,081 | B2 | | 11/2005 | Abels |
| 6,964,565 | B2 | | 11/2005 | Abels et al. .................... 433/10 |
| 7,094,052 | B2 | | 8/2006 | Abels et al. |
| 7,125,249 | B1 | * | 10/2006 | Lauren ............................ 433/9 |
| 7,134,872 | B2 | | 11/2006 | Abels et al. |
| 7,204,691 | B2 | * | 4/2007 | Darling et al. ................ 433/11 |
| 2001/0029007 | A1 | | 10/2001 | Abels ............................ 433/10 |
| 2002/0025500 | A1 | | 2/2002 | Abels et al. |
| 2002/0110771 | A1 | | 8/2002 | Abels et al. |
| 2002/0110772 | A1 | | 8/2002 | Abels et al. |
| 2002/0110773 | A1 | | 8/2002 | Abels et al. |
| 2002/0110774 | A1 | | 8/2002 | Abels et al. |
| 2002/0110775 | A1 | | 8/2002 | Abels et al. .................... 433/11 |
| 2002/0110776 | A1 | | 8/2002 | Abels et al. .................... 433/11 |
| 2002/0110777 | A1 | | 8/2002 | Abels et al. .................... 433/11 |
| 2002/0110778 | A1 | | 8/2002 | Abels et al. |
| 2002/0119414 | A1 | | 8/2002 | Orikasa |
| 2002/0150857 | A1 | | 10/2002 | Orikasa et al. |
| 2002/0187452 | A1 | | 12/2002 | Abels et al. |
| 2003/0008259 | A1 | | 1/2003 | Kuo |
| 2003/0049582 | A1 | | 3/2003 | Abels et al. |
| 2004/0013995 | A1 | | 1/2004 | Spencer ........................ 433/11 |
| 2004/0157186 | A1 | * | 8/2004 | Abels et al. .................... 433/10 |
| 2004/0175667 | A1 | | 9/2004 | Abels et al. .................... 433/10 |
| 2004/0175668 | A1 | | 9/2004 | Abels et al. .................... 433/10 |
| 2004/0185410 | A1 | | 9/2004 | Lai ............................ 433/11 |
| 2005/0186525 | A1 | * | 8/2005 | Abels et al. .................... 433/10 |
| 2005/0196729 | A1 | * | 9/2005 | Jessop et al. ................ 433/229 |
| 2005/0244774 | A1 | | 11/2005 | Abels et al. .................... 433/10 |
| 2005/0244776 | A1 | | 11/2005 | Abels et al. |
| 2005/0255422 | A1 | * | 11/2005 | Cordato ........................ 433/10 |
| 2005/0266268 | A1 | | 12/2005 | Tsuboyama |
| 2005/0266369 | A1 | | 12/2005 | Scommegna et al. |
| 2006/0046223 | A1 | | 3/2006 | Abels et al. .................... 433/10 |
| 2006/0084025 | A1 | | 4/2006 | Abels et al. |
| 2006/0210942 | A1 | * | 9/2006 | Pace et al. ........................ 433/8 |
| 2006/0228663 | A1 | | 10/2006 | Darling et al. |
| 2007/0099145 | A1 | | 5/2007 | Abels |

FOREIGN PATENT DOCUMENTS

| | | | |
|---|---|---|---|
| DE | 202005013890 U1 | | 11/2005 |
| EP | 2005009467 | | 9/2005 |
| GB | 2 017 500 | | 10/1979 |
| JP | 03012147 | | 1/1991 |
| WO | WO 94/00072 | | 1/1994 |
| WO | WO 00/33760 | * | 6/2000 |
| WO | WO 00/76419 | | 12/2000 |
| WO | 2004004592 | | 1/2004 |

OTHER PUBLICATIONS

Paladin, Pam "Colorful Braces Make a Fashion Statement" from the internet URL: http://www.braces.org/braces/news/colorful.cfm.

Fortini, M. et al., "A New Low-Friction Ligation System" Journal of Clinical Orthodontics, vol. 39: No. 08: pp. 464-470 2005 http://www.jco-online.com/archive/article-view.aspx?year=2005&month=08&articlenum=464.

Echols, Michael Dr., "How to Tighten Orthodontic Braces" from the internet URL: http://www.braceface.com/tighten.htm Based on information and belief available, at least as early as Dec. 7, 2004.

Paladin, Pam "Colorful Braces Make a Fashion Statement" from the internet URL: http://www.braces.org/braces/news/colorful.cfm Based on information and belief available, at least as early as Dec. 7, 2004.

Ultradent Products, Inc. "Products & Procedures" Orthodontic Material, 1991-92 Products Brochure, p. 33.

Office Action dated Apr. 6, 2006 cited in U.S. Appl. No. 10/932,634.

NOA dated Aug. 24, 2006 cited in U.S. Appl. No. 10/932,634.

Office Action dated Sep. 3, 2008 cited in U.S. Appl. No. 11/613,767.

* cited by examiner

LIFESTYLE BRACKET SYSTEM HAVING INTERCHANGEABLE LIGATION COVERS

BACKGROUND OF THE INVENTION

1. The Field of the Invention

The present invention relates to orthodontic brackets, more particularly to self-ligating orthodontic brackets that include a base, at least one slot for receiving an arch wire, and a ligating cover.

2. The Relevant Technology

Orthodontics is a specialized field of dentistry that involves the application of mechanical forces to urge poorly positioned, or crooked, teeth into correct alignment and orientation. Orthodontic procedures can be used for cosmetic enhancement of teeth, as well as medically necessary movement of teeth to correct overjets or overbites. For example, orthodontic treatment can improve the patient's occlusion, or enhanced spatial matching of corresponding teeth.

The most common form of orthodontic treatment involves the use of orthodontic brackets and wires, which together are commonly referred to as "braces." Orthodontic brackets, more particularly the orthodontic bases, are small slotted bodies configured for direct attachment to the patient's teeth or, alternatively, for attachment to bands which are, in turn, cemented or otherwise secured around the teeth. Once the brackets are affixed to the patient's teeth, such as by means of glue or cement, a curved arch wire is inserted into the slot of each bracket. The arch wire acts as a template or track to guide movement of the teeth into proper alignment.

There are two distinct classes of orthodontic brackets: those that require the use of ligatures to fasten the arch wire to the bracket, and those that are self-ligating. In brackets of the first class, small ligature wires are typically used to hold the arch wire in a securely seated position in the brackets. Ligatures or some other form of fastening means are essential to ensure that the tensioned arch wire is properly positioned around the dental arch, and to prevent the wire from being dislodged from the bracket slots during chewing of food, brushing of teeth, or application of other forces. One type of commercially available ligature is a small, elastomeric O-ring, which is installed by stretching the O-ring around small wings known as "tie wings" that are connected to the bracket body. Metal ligatures are also used to retain arch wires within the bracket slots.

In an effort to simplify the process of installing braces, a variety of self-ligating brackets have been developed. The term "self-ligating bracket" refers to a class of orthodontic brackets that include some sort of cover, whether separate from or hingedly or slidably attached to the base, which encloses or otherwise retains the arch wire within the slot of the base.

Besides the difficulties associated with the general discomfort of orthodontic brackets, many patients dislike the appearance of installed orthodontic brackets. Most existing orthodontic brackets are formed of metal, and result in a rather particular aesthetic appearance, which some patients dislike. It would be an improvement in the art to provide a self-ligating orthodontic bracket system that allows the patient some flexibility in creating a desired aesthetic look, while still providing ease of use, inexpensive manufacturing, strength, and durability.

BRIEF SUMMARY OF THE PREFFERED EMBODIMENTS

The present invention is directed to an orthodontic bracket system including two or more interchangeable ligation covers and that allows the patient to create a desired aesthetic look. The inventive orthodontic bracket system includes a bracket base, at least one arch wire slot formed in the bracket base adapted to receive an arch wire therein, a first interchangeable ligation cover that is removably attachable to the bracket base and that can be selectively moved relative to the bracket base between an open non-ligating position relative to the arch wire slot and a closed, ligating position relative to the arch wire slot, and a second interchangeable ligation cover. The second interchangeable ligation cover is of a different color and/or formed of a different material relative to the first interchangeable ligation cover. Attachment means are provided so that the first and second interchangeable ligation covers may be releasably attached to the bracket base. The bracket system and releasable attachment means advantageously allow the practitioner to remove the first interchangeable ligation cover and replace it with a second (or another) interchangeable ligation cover that is of a different color and/or formed of a different material to create a desired aesthetic appearance.

The inventive bracket system allows the patient or practitioner to select one or more bracket bases of a desired color and material (e.g., metal, a ceramic, glass, or a colored or uncolored polymeric resin), and then select a first interchangeable ligation cover of a desired color and material (e.g., metal, glass, or a colored or uncolored polymeric resin). The selected interchangeable ligation cover may later be removed and replaced with an interchangeable cover of a different color or material, while the bracket base may advantageously remain bonded to the tooth. Such a system advantageously provides the practitioner and patient with flexibility in creating and changing the aesthetic appearance of each individual installed bracket, and the overall look of the plurality of brackets installed on a plurality of teeth.

Exemplary suitable metallic materials that may be used to form the bracket base and/or the interchangeable ligation covers include, but are not limited to, stainless steel, stainless steel alloys, titanium, and nickel-titanium alloys.

Exemplary ceramic materials that may be used to form the bracket base include, but are not limited to, aluminous oxide, zirconia, and porcelain.

Exemplary polymeric resin materials that may be used to form the bracket base and/or the interchangeable ligation covers include, but are not limited to, polyamides (e.g., crystalline or amorphous), acetal polymers, polyetherimides, polycarbonates, polyarylether ketones, polysulfones, and polyphenylsulfones.

According to one embodiment, the interchangeable ligation cover is impregnated and/or coated with a medicament (e.g., fluoride). Such an embodiment advantageously allows the orthodontic practitioner to replace the interchangeable ligation cover once the medicament within the first or preceding interchangeable ligation cover has been depleted. Such an embodiment allows for continued administration of the medicament as the interchangeable ligation cover is easily replaced without requiring removal of the bracket base (i.e., it may be performed in a matter of seconds).

Exemplary kits according to the invention include a plurality of bracket bases and a plurality of interchangeable ligation covers. Each interchangeable ligation cover included within the kit is attachable to any of the bracket bases. At least one interchangeable ligation cover within the kit is of a different color and/or formed of a different material relative to at least one other of the interchangeable ligation covers. The inventive kit advantageously allows a patient and practitioner to create a desired aesthetic appearance by mixing and/or matching different bracket bases and interchangeable ligation covers, as desired.

A related method of using the orthodontic bracket systems and kits involves selecting a bracket base from a plurality of bracket bases of different colors and/or materials, selecting a first interchangeable ligation cover from a plurality of covers of different colors and/or materials, attaching the selected cover to the selected bracket so as to form an orthodontic bracket, bonding the bracket to a patient's tooth, subsequently removing the first interchangeable ligation cover from the bracket base of the orthodontic bracket, and replacing the first interchangeable ligation cover with a second interchangeable ligation cover of a different color and/or formed of a different material relative to the first interchangeable ligation cover. The method advantageously allows a patient and practitioner to create and then change the aesthetic appearance of the brackets installed on the patient's teeth. Furthermore, changing the aesthetic appearance by replacing the ligation cover may advantageously be performed without requiring removal of the bracket base from the tooth to which it is bonded.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The invention generally relates to an orthodontic bracket system including a bracket base, at least one arch wire slot formed in the bracket base, at least two interchangeable ligation covers, and attachment means for releasably attaching the first and second interchangeable ligation covers to the bracket base so as to allow the patient and practitioner to change and/or create any desired aesthetic appearance. When attached to the bracket base, each interchangeable ligation cover can be selectively moved relative to the bracket base between an open non-ligating position relative to the arch wire slot and a closed, ligating position relative to the arch wire slot. The second interchangeable ligation cover is advantageously of a different color and/or formed of a different material relative to the first interchangeable ligation cover such that the practitioner is able to remove one ligation cover and replace it with another cover, as desired. Advantageously, interchanging of the ligation covers is easily performed without first requiring removal of the bracket base from the patient's tooth.

II. Exemplary Orthodontic Bracket Systems

Figure 1:
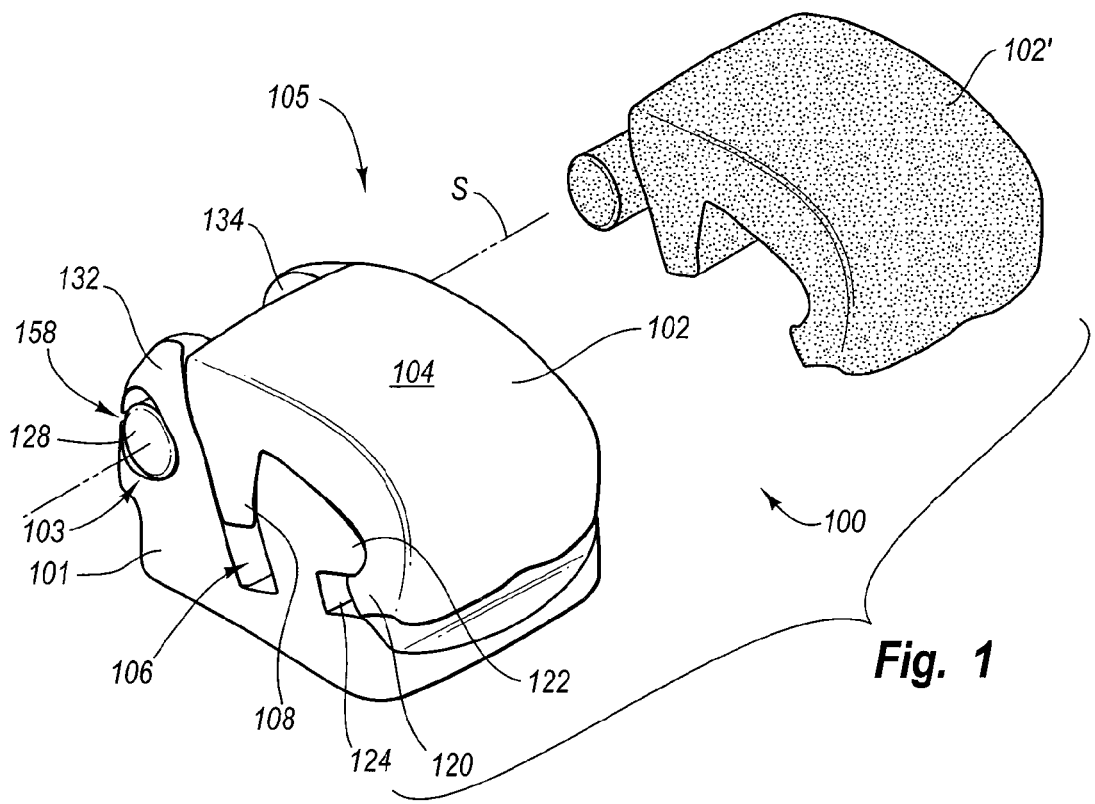
FIG. 1 is a perspective view of an exemplary orthodontic bracket system of the present invention including a bracket base and at least two interchangeable ligation covers.
Figure 2:
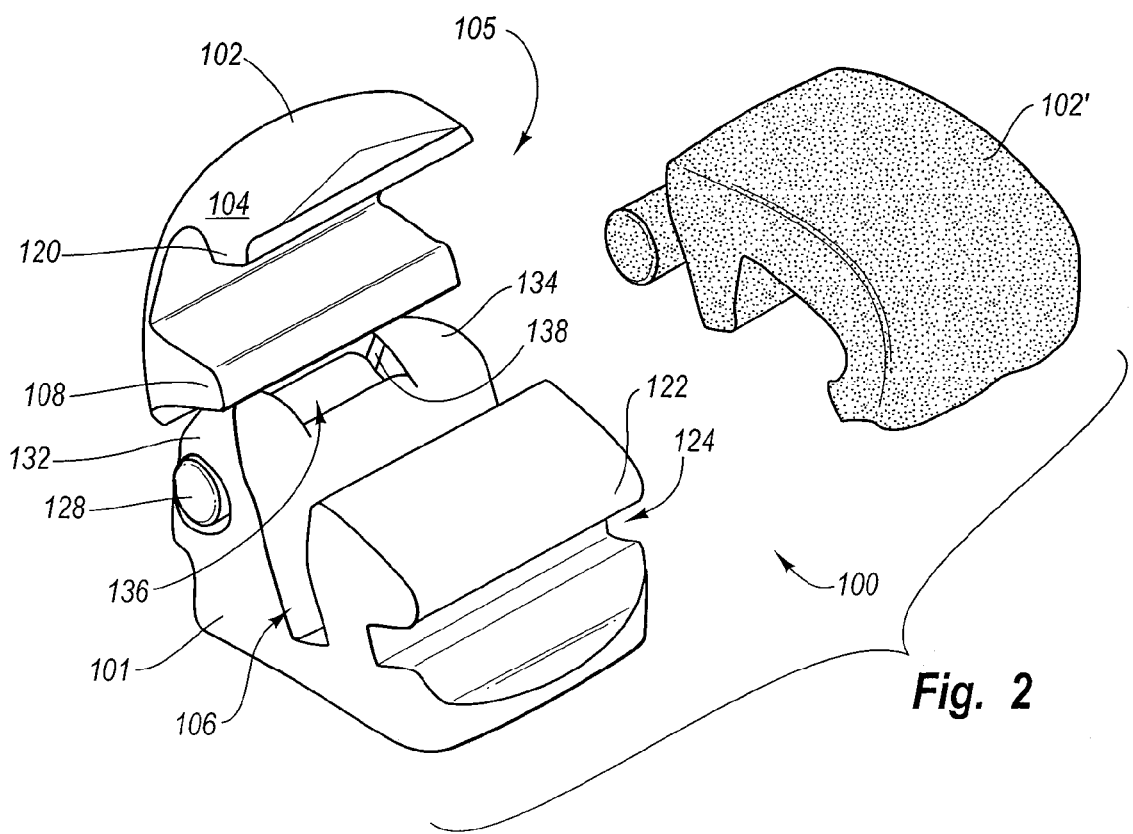
FIG. 2 is a perspective view of the orthodontic bracket system of FIG. 1 with the interchangeable ligation cover attached to the bracket base in an open configuration such that the arch wire slot is unoccluded by the attached ligation cover.
Figure 3:
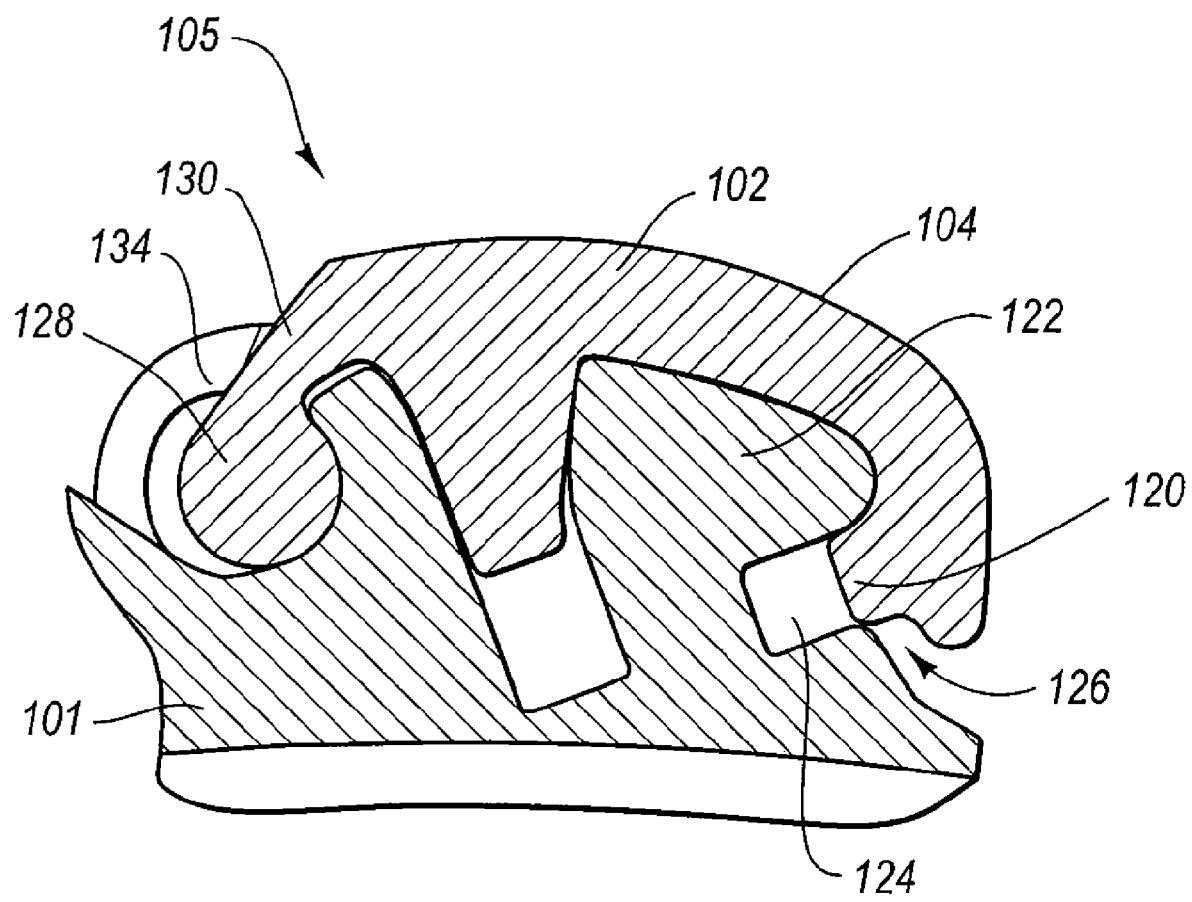
FIG. 3 is a cross sectional view of the orthodontic bracket shown as part of the system of FIGS. 1 and 2.

FIGS. 1-3 illustrate an exemplary orthodontic bracket system 100. The bracket base 101 and first interchangeable ligation cover 102 (or second interchangeable ligation cover 102')

may be assembled to form an orthodontic bracket 105. As assembled, the base 101 and cover 102 are pivotally connected to each other via a joint 103 which has a horizontal pivot axis S about which first interchangeable ligation cover 102 can be pivoted from its completely closed and latched position shown in FIG. 1 to an open position shown in FIG. 2. It is to be understood that the bracket base 101 can alternatively be assembled with second interchangeable ligation cover 102' to form an alternative orthodontic bracket.

In the embodiment shown, first interchangeable ligation cover 102 comprises a cover having a smooth, curved outer surface 104. This prevents or reduces potential injury and discomfort to the patient, as well as the tendency for food or other foreign substances to catch or adhere to the orthodontic bracket 105.

As further illustrated in FIG. 1, the first interchangeable ligation cover 102, while in a completely closed or latched state relative to the bracket base 101, covers or occludes a slot 106 designed to receive therein an arch wire (not shown). The interchangeable ligation cover 102 is advantageously provided with a bearing extension 108 designed to bear against and hold an arch wire in slot 106 and/or auxilliary slot 124 when the interchangeable ligation cover 102 is closed or latched relative to the bracket base 101.

The interchangeable ligation cover 102 can be latched or locked to the bracket base 101 in order to maintain the interchangeable ligation cover 102 in a closed or latched state by means of a latch projection 120 provided at an end of the interchangeable ligation cover 102 distal to the joint 103. The latch projection 120 generally extends toward the bracket base 101 and is configured so as to snap over a latch bump 122 provided at the bracket base 101 in order to mechanically latch the interchangeable ligation cover 102 to the bracket base 101.

In the open position (FIG. 2), first interchangeable ligation cover 102 advantageously opens sufficiently so as to not occlude slot 106. For example, in one embodiment, cover 102 may rotate sufficiently when open so as to form an angle of at least about 60°, more preferably at least about 90° with bracket base 101. Furthermore, the ligation cover may also be configured such that it is not biased to an occluding or closed position relative to the arch wire slot within the bracket base 101. Such features are advantageous as they provide improved access when inserting or removing an arch wire from slot 106 as compared to a configuration where cover 102 is biased to an occluding or closed position, or where the ligation cover still occludes or covers slot 106, even when fully open.

Interchangeable ligation cover 102 also includes a pair of spigots 128 which are connected to the interchangeable ligation cover 102 by means of a connection web 130 (perhaps best seen in FIG. 3). In one embodiment, spigots 128 have a cylindrical cross-section. The spigots 128 are each received in a respective link guide 132 and 134 connected to bracket base 101. The spigots 128 and link guides 132 and 134 together comprise at least a portion of joint 103. The interaction between the spigots 128 and link guides 132 and 134 allow the interchangeable ligation cover 102 to be rotated about the pivot axis S between the open and closed positions. Joint 103 is one example of attachment means for releasably attaching interchangeable ligation cover 102 to bracket base 101.

The link guides 132 and 134 are in a spaced-apart relationship and include opposing inner surfaces that together define a guide recess 136. The inner surfaces of the link guides 132 and 134 also include chamfers 138. In use, the connection web 130 of the interchangeable ligation cover 102 can be inserted into the guide recess 136 while closing the interchangeable ligation cover 102 relative to the bracket base 101. The joint and its operation is described in greater detail in U.S. Pat. No. 6,964,565, entitled TWO-PART ORTHODONTIC BRACKET, which is hereby incorporated by reference.

Figure 4A:
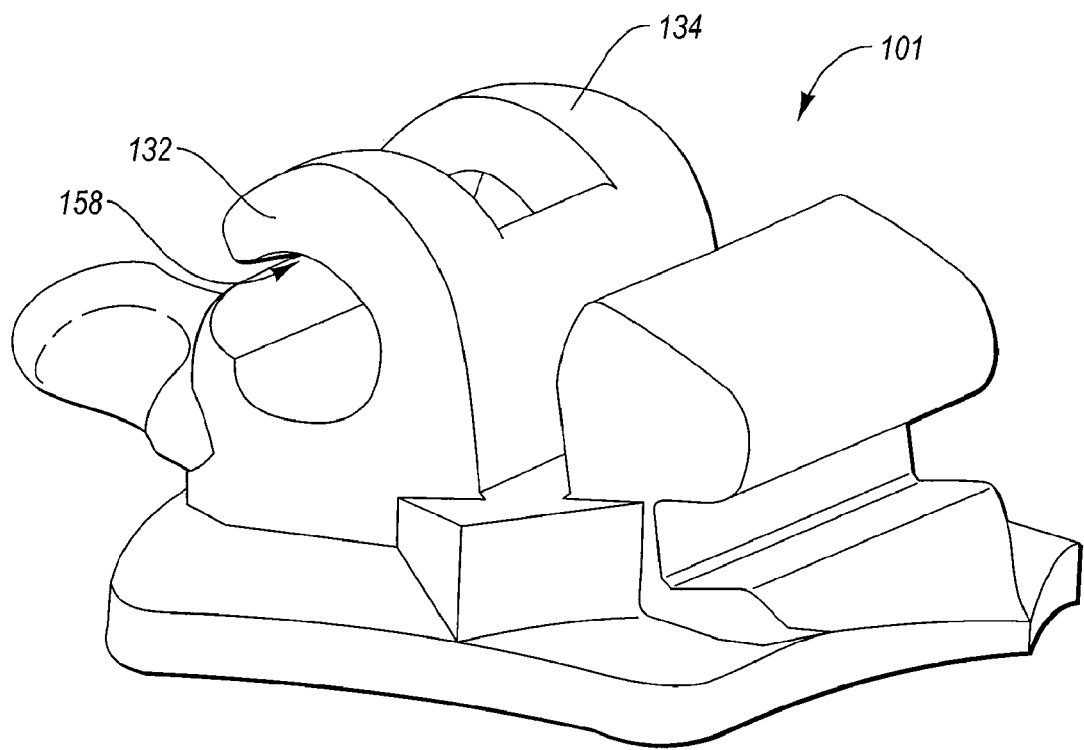
FIG. 4A is a perspective view of an exemplary bracket base.
Figure 4B:
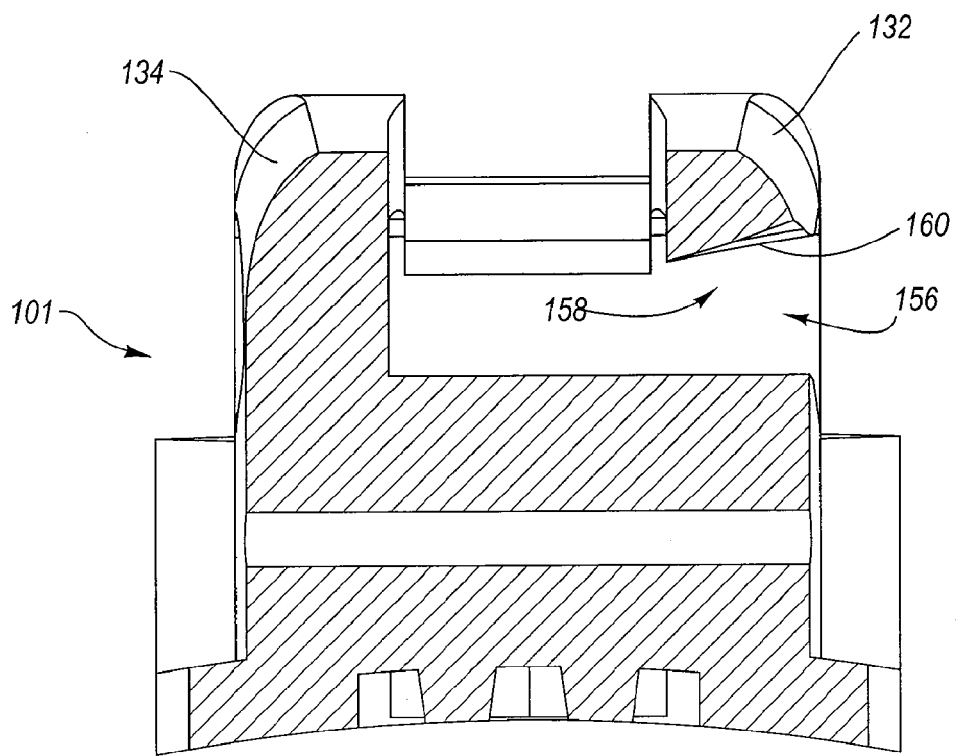
FIG. 4B is an elevation view of the rear of the bracket base of FIG. 4A showing a ramped passage opening in one of the two link guides for facilitating attachment of an interchangeable ligation cover to the bracket base.
Figure 4C:
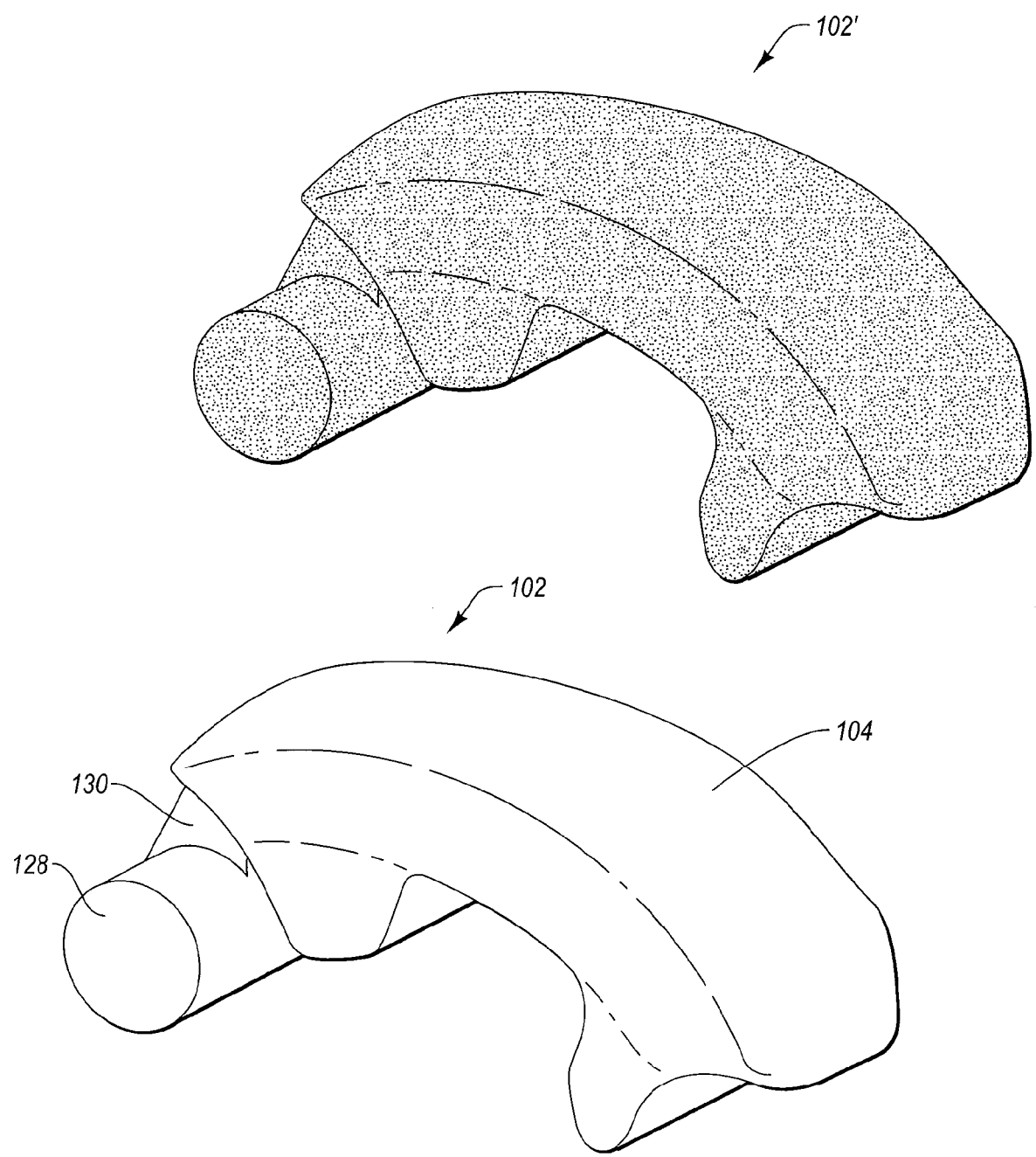
FIG. 4C is a perspective view of two exemplary interchangeable ligation covers.

FIGS. 4A-4C illustrate bracket base 101 and interchangeable ligation covers 102 and 102' of the orthodontic bracket system 100 separately. FIG. 4A shows orthodontic bracket base 101. FIG. 4B shows a rear elevation view of bracket base 101, while FIG. 4C shows unattached exemplary first and second interchangeable ligation covers 102 and 102', respectively. As shown, second interchangeable ligation cover 102' is advantageously of a different color and/or material relative to cover 102.

To facilitate assembly of interchangeable ligation cover 102 (or 102') with bracket base 101, at least one of link guides 132 and 134 may advantageously be provided with a passage opening 156 which is dimensioned such that the spigots 128 can be pushed therethrough along the pivot axis S when the interchangeable ligation cover 102 is in a completely open position relative to bracket base 101 (FIG. 2). Link guide 132 further includes an auxilliary passage 158 having a ramped surface 160 that is inclined so as to cause the link guide 132 to be slightly stretched elastically so as to permit passage of connection web 130 through auxilliary passage 158. After connection web 130 is fully inserted through auxiliary passage 158, link guide 132 snaps back to its original configuration, thereby forming a snap connection that captively retains interchangeable ligation cover 102 to bracket base 101.

To remove the interchangeable ligation cover 102, the orthodontic practitioner may use the reverse procedure. The link guide 132 is slightly stretched elastically so as to permit passage of the connection web 130 out of auxiliary passage 158, detaching the interchangeable ligation cover 102 from base 101. Once the ligation cover is detached, link guide 132 snaps back to its original configuration.

It should be appreciated that the joint or attachment mechanism for releasably attaching the interchangeable ligation cover to the bracket base can be realized in other manners. One alternative attachment mechanism is described below in conjunction with FIGS. 5-9. Other joint mechanisms or attachment means will be apparent to one skilled in the art. It is only necessary that the interchangeable ligation cover 102 (and 102') is readily attachable and removable from the bracket base 101, so as to allow an orthodontic practitioner to replace a first interchangeable ligation cover 102 with a second interchangeable ligation cover 102', as desired.

Figure 5:
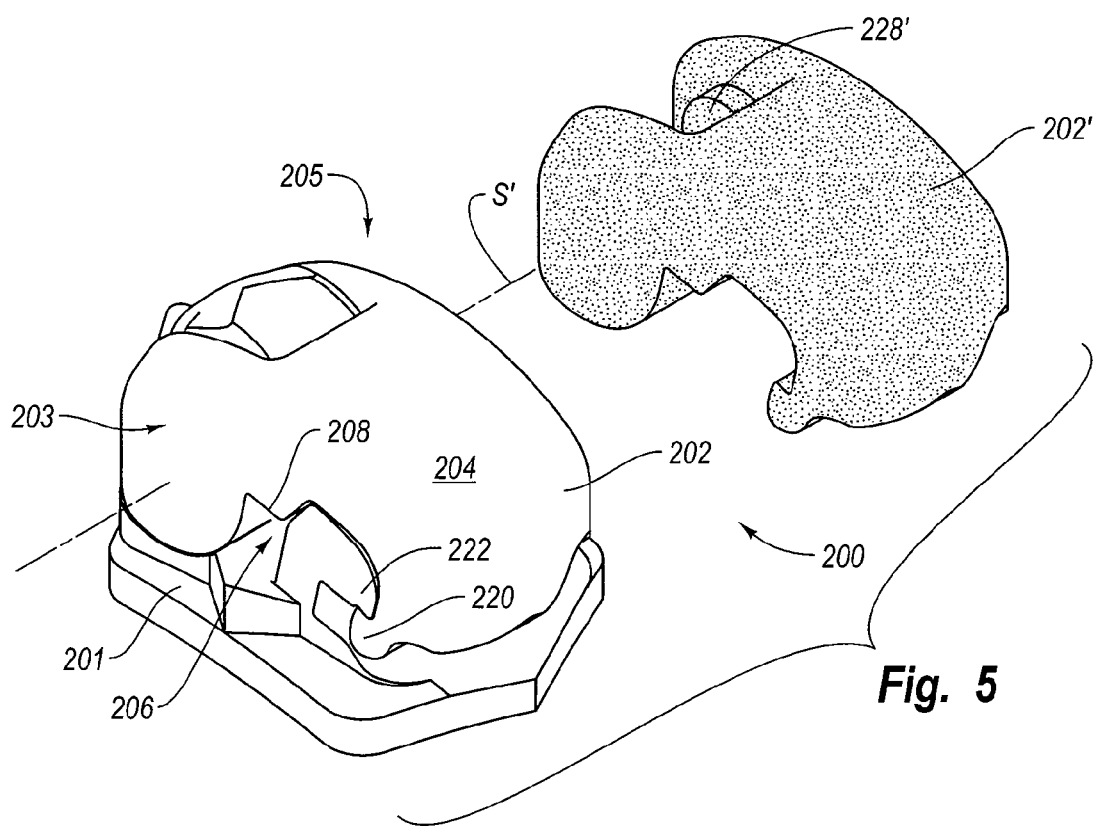
FIG. 5 is a perspective view of an alternative orthodontic bracket system of the present invention including a bracket base and at least two interchangeable ligation covers.
Figure 6:
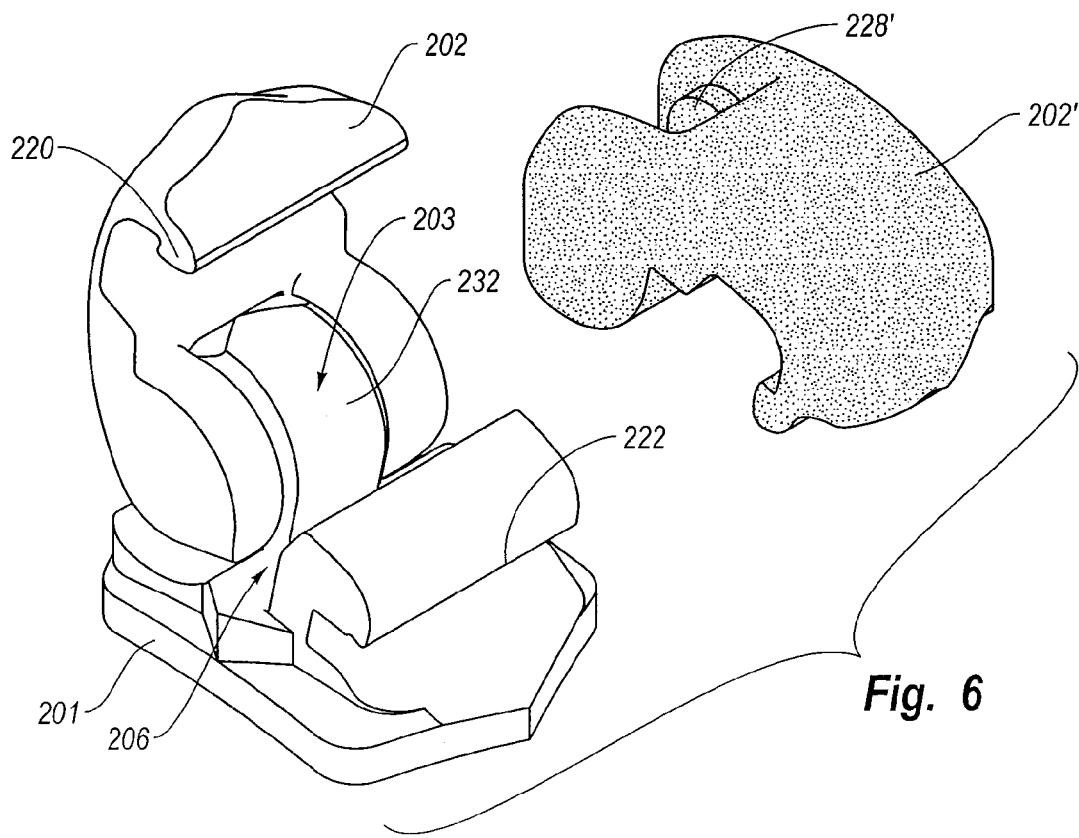
FIG. 6 is a perspective view of the orthodontic bracket system of FIG. 5 with an interchangeable ligation cover attached to the bracket base in an open configuration such that the arch wire slot is unoccluded by the attached ligation cover.

FIGS. 5-6 illustrate an alternative exemplary orthodontic bracket system 200. The bracket base 201 and first interchangeable ligation cover 202 (or second interchangeable ligation cover 202') may be assembled to form an alternative orthodontic bracket 205. Similar to bracket 105, bracket 205 includes an arch wire slot 206, a bearing extension 208, a latch projection 220, and a latch bump 222. Bracket 205 presents a smooth, curved outer surface 204 along cover 202. In addition, there are no outwardly exposed spigots, but rather only a smooth outer surface along the sides of joint 203. The smooth outer surface surrounding joint 203 is advantageous as it reduces the possible locations where food or other foreign matter may become lodged. Joint 203 is an example of alternative means for releasably attaching interchangeable ligation cover 202 (or 202') to bracket base 201. Joint 203 also has a horizontal pivot axis S' about which first interchangeable ligation cover 202 can be pivoted from its completely closed and latched position shown in FIG. 5 to an open and unoccluded position shown in FIG. 6.

Figure 7A:
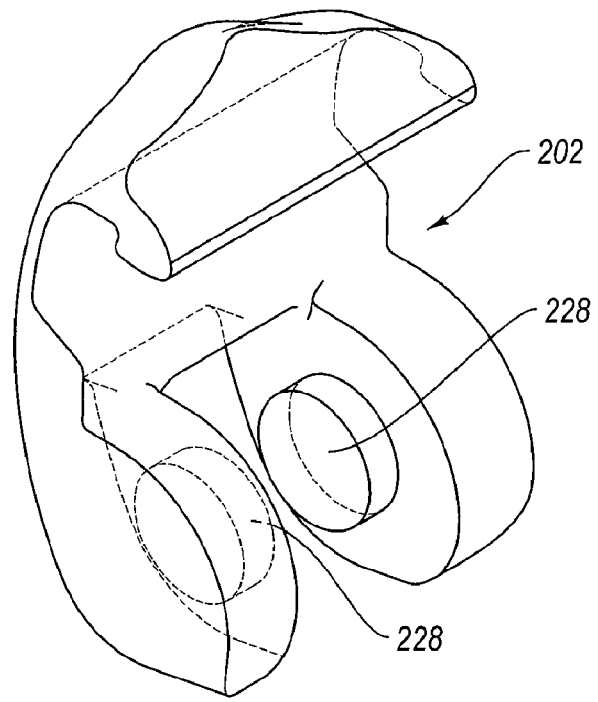
FIG. 7A is a perspective view of one of the alternative interchangeable ligation covers from the system of FIGS. 5 and 6.
Figure 9:
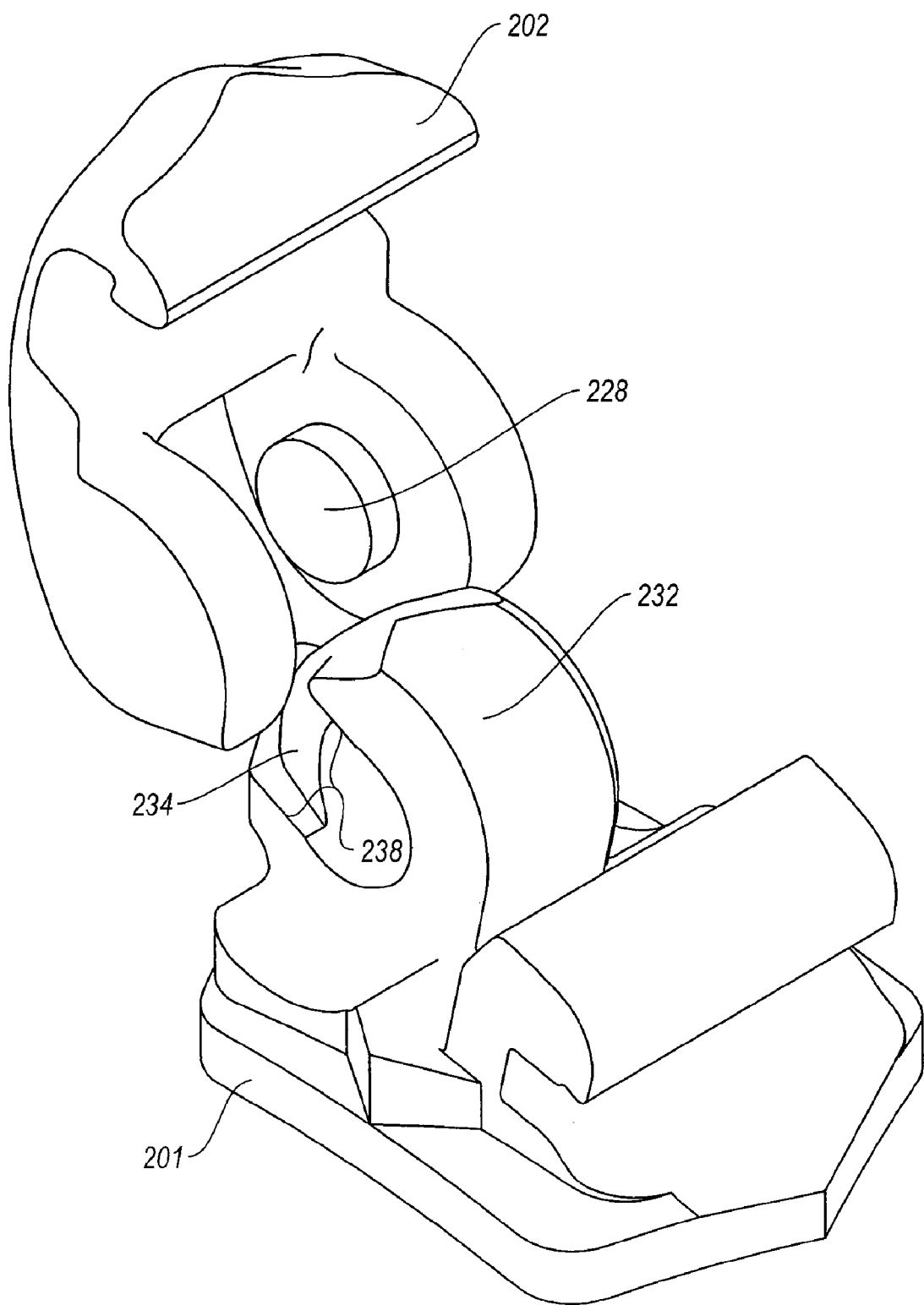
FIG. 9 is a perspective view of the interchangeable ligation cover and bracket base of FIGS. 7A and 8A, respectively, with the interchangeable ligation cover aligned in a position for attachment to the bracket base.

Interchangeable ligation covers 202 and 202' each include a pair of inwardly oriented cylindrical pins 228, 228' (perhaps best seen in FIGS. 7A and 9). When cover 202 is attached to base 201, pins 228 are each received in opposite sides of a single centrally located link guide 232 connected to bracket base 201. The pins 228 and link guide 232 together comprise at least a portion of joint 203. The interaction between the pins 228 and link guide 232 allow the interchangeable ligation cover 202 to be rotated about the pivot axis S' between the open and closed positions. Joint 203 is another example of attachment means for releasably attaching an interchangeable ligation cover to a bracket base.

Figure 8A:
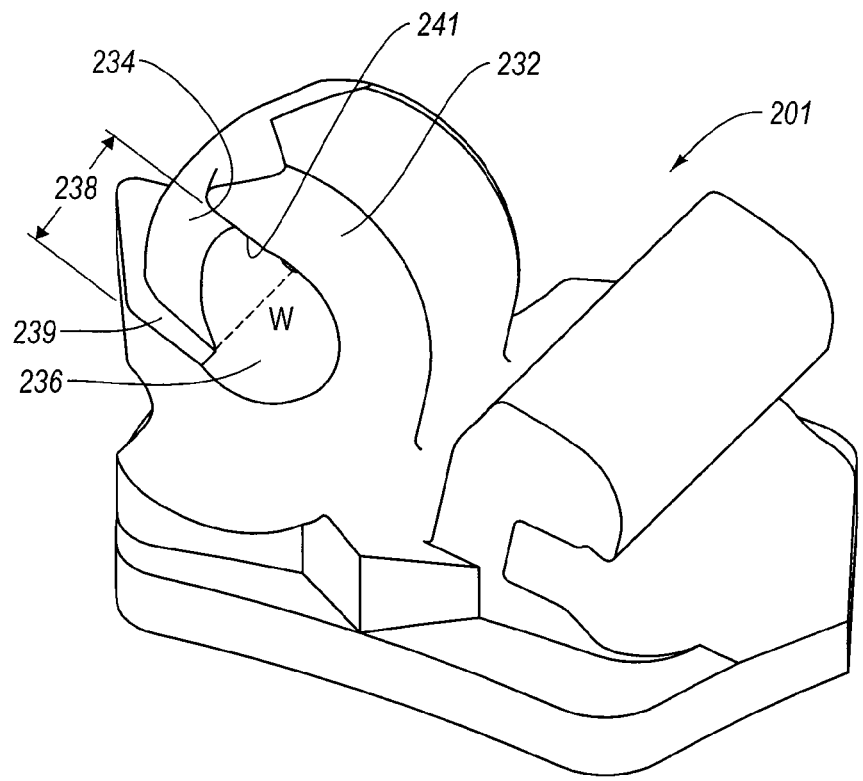
FIG. 8A is a perspective view of the bracket base that forms part of the system of FIGS. 5 and 6.

Pins 228 are connected to cover 202 so as to be in a spaced-apart relationship and are oriented inwardly relative to one another. As seen in FIG. 8A, the outer surfaces on either side of link guide 232 also include sloped guide channels 238 defined by a lower sloped surface 239 and an upper sloped surface 241. In order to attach interchangeable ligation cover 202 to base 201, the cylindrical pins 228 of the interchangeable ligation cover 202 are to be inserted into the guide channels 238 on either side of link guide 232 while pressing the interchangeable ligation cover 202 so as to force pins 228 along sloped guide channels 238 and into substantially cylindrical guide recess 236. Guide recess 236 may advantageously be a substantially cylindrical recess with the outer edges of the recess defined by an interior surface of link guide 232.

Figure 7B:
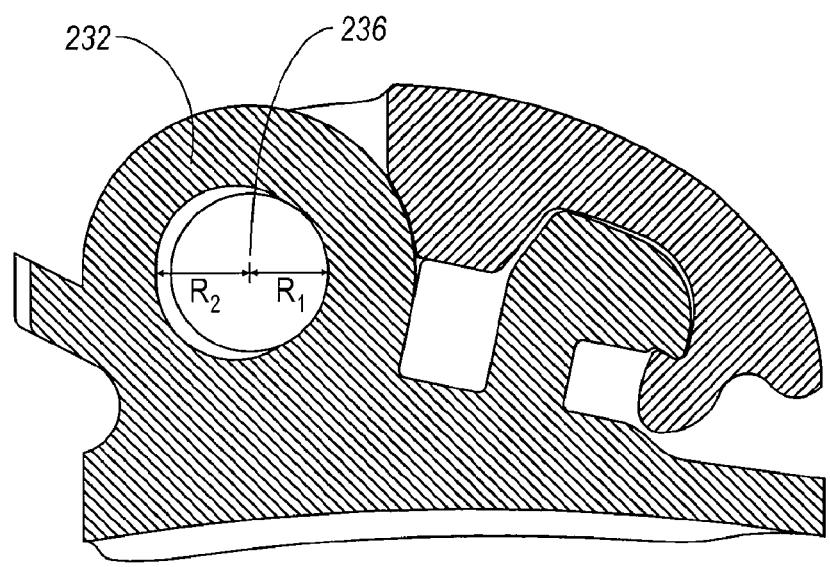
FIG. 7B is a cross sectional view of the orthodontic bracket that forms part of the system shown in FIGS. 5 and 6.

As perhaps best seen in FIG. 7B, guide recess 236 may be slightly assymetrical in cross section so as to better accept cylindrical pins 228. In other words, the radius R1 of a front portion of recess 236 is less than a radius R2 of a rear portion of recess 236. Rear portion radius R2 corresponds to that portion of the recess 236 which first receives pins 228 during attachment of cover 202 to base 201. Such a configuration is particularly helpful when attaching or detaching cover 202 from base 201, as it provides something of a tolerance (i.e., play) when inserting or removing pins 228 from link guide 232.

Figure 8B:
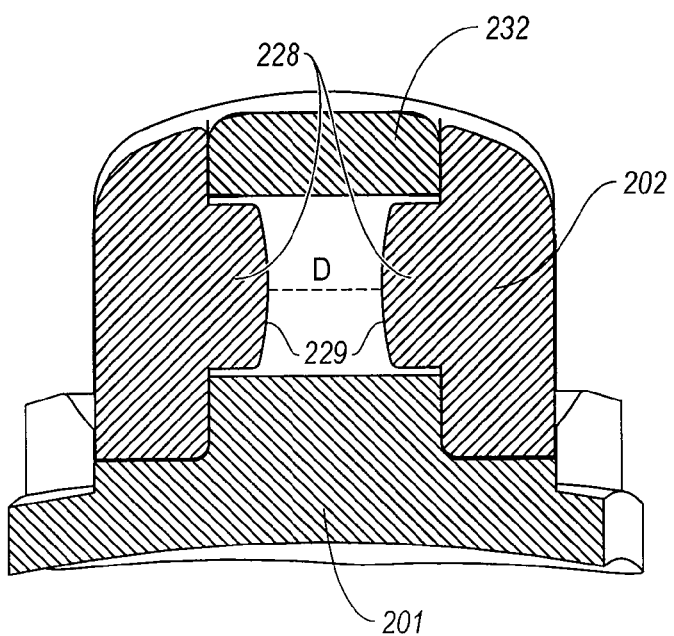
FIG. 8B is an elevation view of the rear of the orthodontic bracket of FIG. 7B.

A locking member 234 is defined by the portion of link guide 232 that is between channels 238. The width W of this locking member 234 is advantageously slightly greater than the distance D between inwardly oriented spaced apart pins 228 (FIGS. 8A and 8B). Furthermore, as seen in FIG. 8B, each pin 228 may advantageously include a convex outer surface 229 which reduces the amount of material that must flex in order to force pins 228 over locking member 234, as well as reducing the overall required assembling/dis-assembling force (i.e., contact occurs between the sides of locking member 234 and the outermost points of outer surfaces 229, rather than along the full outer surface 229). During attachment of cover 202 to base 201, pins 228 and the adjacent portion of cover 202 are elastically stretched or flexed so as to accommodate the width of locking member 234 of link guide 232. After pins 228 slide past locking member 234 (within channels 238) and are fully inserted within guide recess 236, pins 228 snap back to their original configuration, thereby forming a snap connection that captively retains interchangeable ligation cover 202 to bracket base 201.

To remove the interchangeable ligation cover 202, the orthodontic practitioner may use the reverse procedure. With the cover 202 in the open position, the pins 228 can be slightly stretched elastically so as to permit passage of the pins 228 out of guide recess 236, and into channels 238, detaching the interchangeable ligation cover 202 from base 201. Once the ligation cover is slid out of channels 238, pins 228 snap back to their original configuration.

This particular joint configuration is advantageous as it allows for very simple assembly and dis-assembly of the orthodontic bracket, which is particularly helpful as the orthodontic brackets are very small (e.g., length of about 4 mm, width of about 2 mm, height of about 3 mm). As such, it can be quite difficult to orient the interchangeable ligation cover 102 or 102' relative to the bracket base as needed when assembling the bracket. The embodiment including interchangeable ligation cover 202 or 202' only requires that the cover be aligned with the base, and then pressed in. In other words, no twisting is required during the aligning process. As such, the configuration of system 200 may be preferred over system 100.

The bracket base and interchangeable ligation covers of the orthodontic bracket system may be formed of various materials. According to one embodiment, the bracket base is formed of at least one of a ceramic, glass, metal, or a polymeric resin. Preferred ceramic materials include, but are not limited to, aluminous oxide, zirconia, and porcelain. According to one embodiment, the interchangeable ligation covers are formed of at least one of glass, metal, or a polymeric resin. Examples of suitable metals from which the bracket base or interchangeable ligation covers may be formed include, but are not limited to, stainless steel, stainless steel alloys, titanium, and nickel-titanium alloys.

Preferred polymeric resin materials from which the bracket base and/or interchangeable ligation covers may be formed include numerous thermoplastic materials. Examples of suitable thermoplastic materials include, but are not limited to, polyamides (crystalline or amorphous), acetal polymers, polyetherimides, polycarbonates, polyarylether ketones, polysulfones, and polyphenylsulfones.

Specific exemplary polymeric resin materials useful in forming orthodontic bracket bases and/or interchangeable ligation covers include TROGAMID, a crystalline polyamide manufactured by Degussa AG, located in Germany; GRILAMID, an amorphous polyamide manufactured by EMS-CHEMIE AG, located in Germany; PEEK, a polyarylether ketone manufactured by Victrex USA, Inc., located in Greenville, S.C.; and RADEL, a polyphenylsulfone manufactured by Solvoy S.A., located in Brussels, Belguim.

Additional suitable polymeric resin materials and specific characteristics of the above polymeric resin materials and orthodontic bracket components formed therefrom are disclosed in U.S. Pat. No. 7,247,019 entitled ORTHODONTIC BRACKETS MADE FROM POLYMERIC MATERIALS THAT IMPART DESIRED STRENGTH PROPERTIES, and U.S. application Ser. No. 11/045,948, filed Jan. 28, 2005, and entitled ORTHODONTIC BRACKETS COATED TO INCREASE RESISTANCE TO WEAR AND DEFORMATION, both of which are hereby incorporated by reference.

Figure 12A:
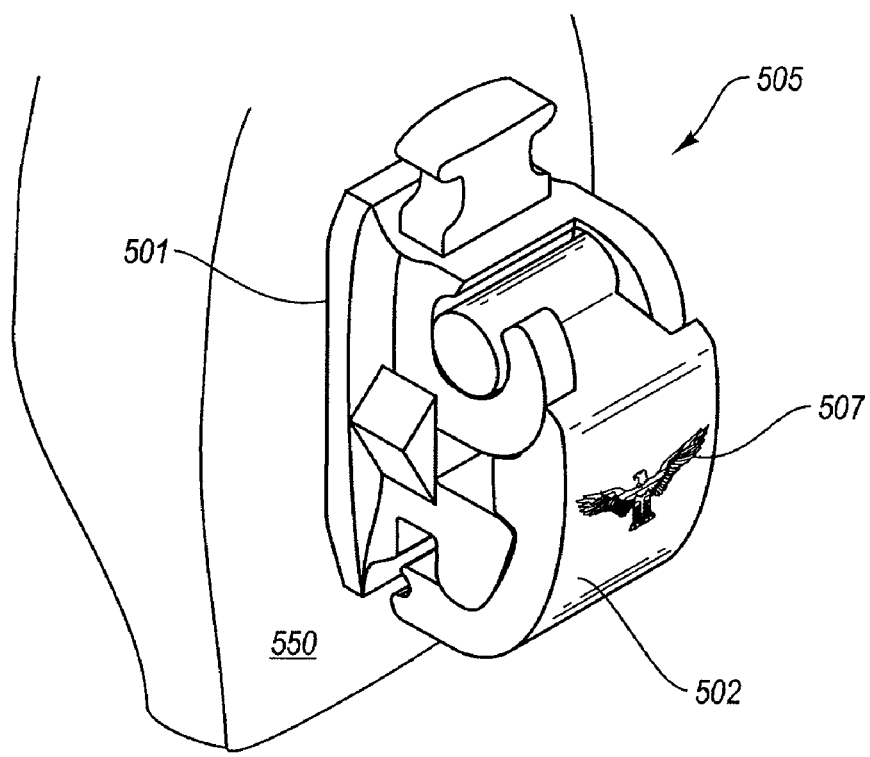
FIG. 12A is a perspective view of an orthodontic bracket illustrating a graphic on the interchangeable ligation cover.
Figure 12B:
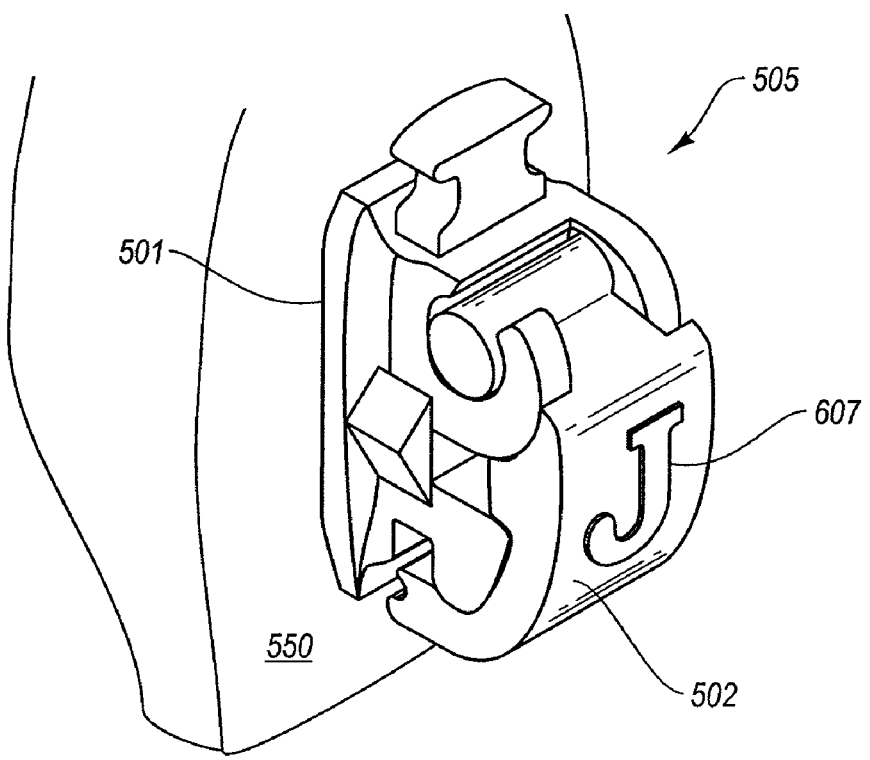
FIG. 12B is a perspective view of an orthodontic bracket illustrating a figure on the interchangeable ligation cover.

According to one embodiment, the interchangeable ligation covers may be colored through incorporation of a dye or pigment into the forming material, especially where the ligation covers are formed from glass or a polymeric resin material. The colored dye or pigment may comprise any desired color (e.g., red, white, blue, green, orange, black, yellow, purple, tooth colored, colorless, etc.). Alternatively, the interchangeable ligation covers may include a colored coating, especially where it is desired to color the covers, and the covers are formed from metal. Such a coating (e.g., a ceramic) may give the interchangeable ligation cover any desired color. Graphics or figures may also be added, as desired. FIG. 12A illustrates a graphic 507 on interchangeable ligation cover 502. FIG 12B illustrates a FIG 607 on interchangeable ligation cover 502. Additional detail and methods of either incorporating a dye or pigment into the forming material or applying a coating which may be colored are disclosed in U.S. application Ser. No. 10/932,634, filed Sep. 2, 2004, and entitled COLORED ORTHODONTIC BRACKETS, hereby incorporated by reference with respect to its disclose of incorporating a colorant into a bracket forming material and applying a coating which may be colored, and U.S. application Ser. No. 11/045,948, filed Jan. 28, 2005, and entitled ORTHODONTIC BRACKETS COATED TO INCREASE RESISTANCE TO WEAR AND DEFORMATION, already incorporated by reference.

Figure 12C:
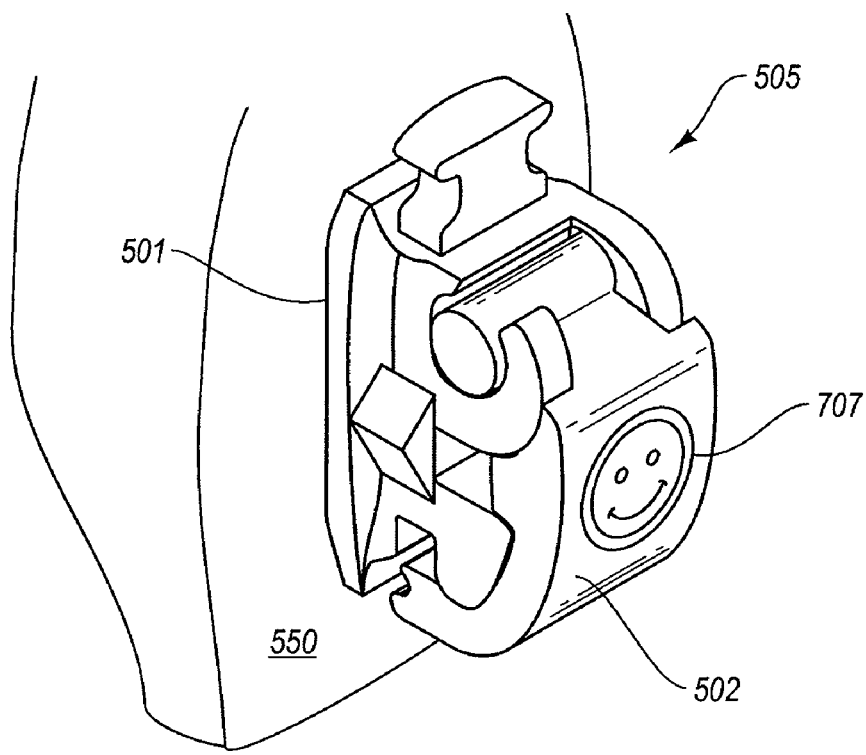
FIG. 12C is a perspective view of an orthodontic bracket illustrating a decal on the interchangeable ligation cover.
Figure 12D:
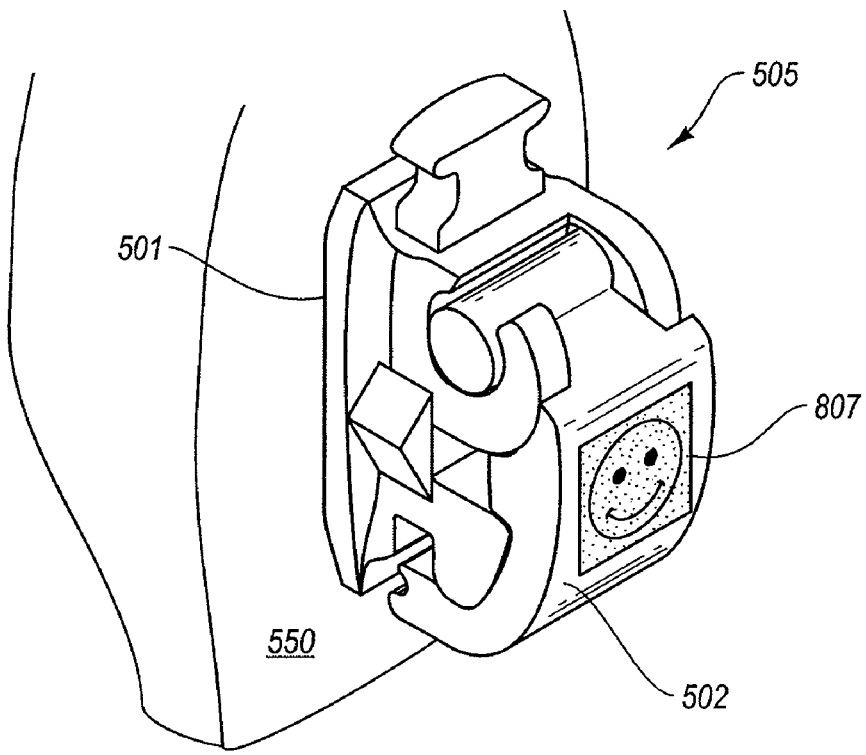
FIG. 12D is a perspective view of an orthodontic bracket illustrating a sticker on the interchangeable ligation cover.
Figure 12E:
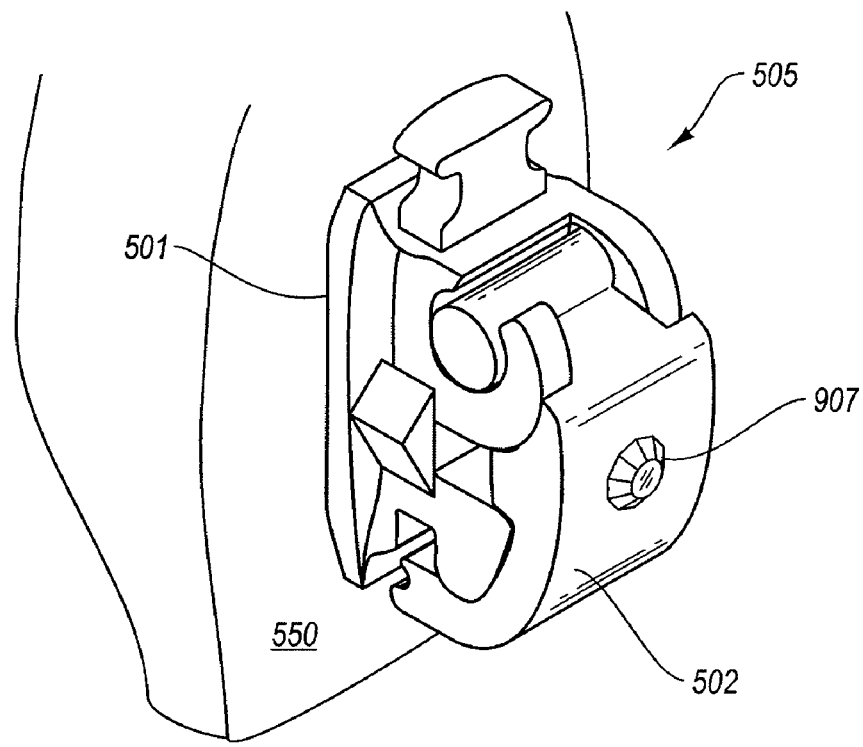
FIG. 12E is a perspective view of an orthodontic bracket illustrating a jewel on the interchangeable ligation cover.
Figure 12F:
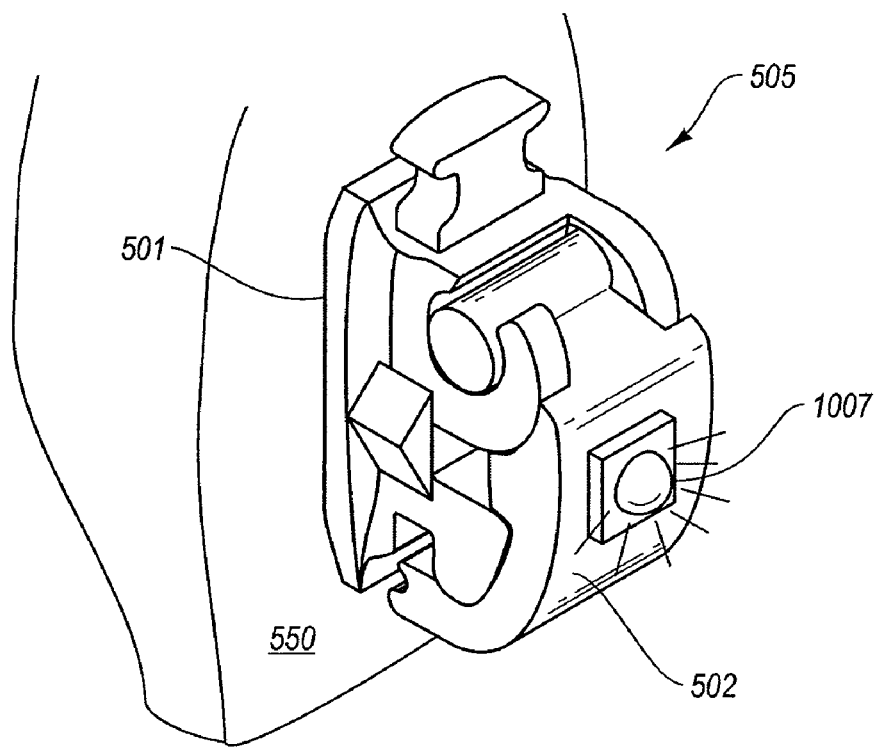
FIG. 12F is a perspective view of an orthodontic bracket illustrating an LED on the interchangeable ligation cover.

Decals, stickers, jewelry, or even small LED lights may be incorporated into or applied over the interchangeable ligation covers. FIG 12C illustrates a decal 707 on interchangeable ligation cover 502. FIG 12D illustrates a sticker 807 on interchangeable ligation cover 502. FIG 12E illustrates a jewels 907 on interchangeable ligation cover 502. FIG 12F illustrates an LED 1007 on interchangeable ligation cover 502. Such features, as well as high contrast colors (i.e., colors providing a high degree of contrast against the teeth, for example, fluorescent and/or bright colors) may be particularly desirable to those patients wishing to draw attention to their brackets. Other patients may instead want to minimize the appearance of their orthodontic brackets, and may choose for example, colorless (i.e., clear) or tooth colored ligation covers. The inventive bracket system advantageously allows each patient and practitioner to tailor the aesthetic appearance of their bracket system to their particular tastes, and to change the appearance, if and when desired.

The inventive orthodontic bracket system provides a great degree of flexibility to both the patient and the practitioner to select the interchangeable ligation covers they desire, and to allow them to change the configuration without requiring removal of the bracket bases (i.e., the interchangeable ligation covers can be removed and replaced while the bracket base remains bonded to the tooth). Furthermore, it will be noted that when installed, the ligation cover largely hides the underlying bracket base from view. Such a characteristic is advantageous as it allows the user to create and change the appearance of the ligation covers while minimizing any color clashing or mismatching which might otherwise be undesirable between the ligation cover and the bracket base. This is particularly advantageous when replacing one or more interchangeable ligation covers while leaving the bracket bases still bonded to the teeth.

The interchangeable ligation covers may advantageously be impregnated and/or coated with a medicament (e.g., fluoride). Such an embodiment allows the practitioner to replace a first interchangeable ligation cover with a new, second interchangeable ligation cover once the medicament within the first interchangeable ligation cover has been depleted. Such a replacement can be performed quickly and easily with little discomfort to the patient as removal and rebonding of the bracket base is not required. Administration of fluoride may be particularly advantageous during orthodontic treatment involving the use of brackets as it can be quite difficult for a patient to maintain clean teeth during the orthodontic treatment. Administration of fluoride may at least partially offset any tendency for increased tooth decay during such treatment.

III. Exemplary Kits

Figure 10:
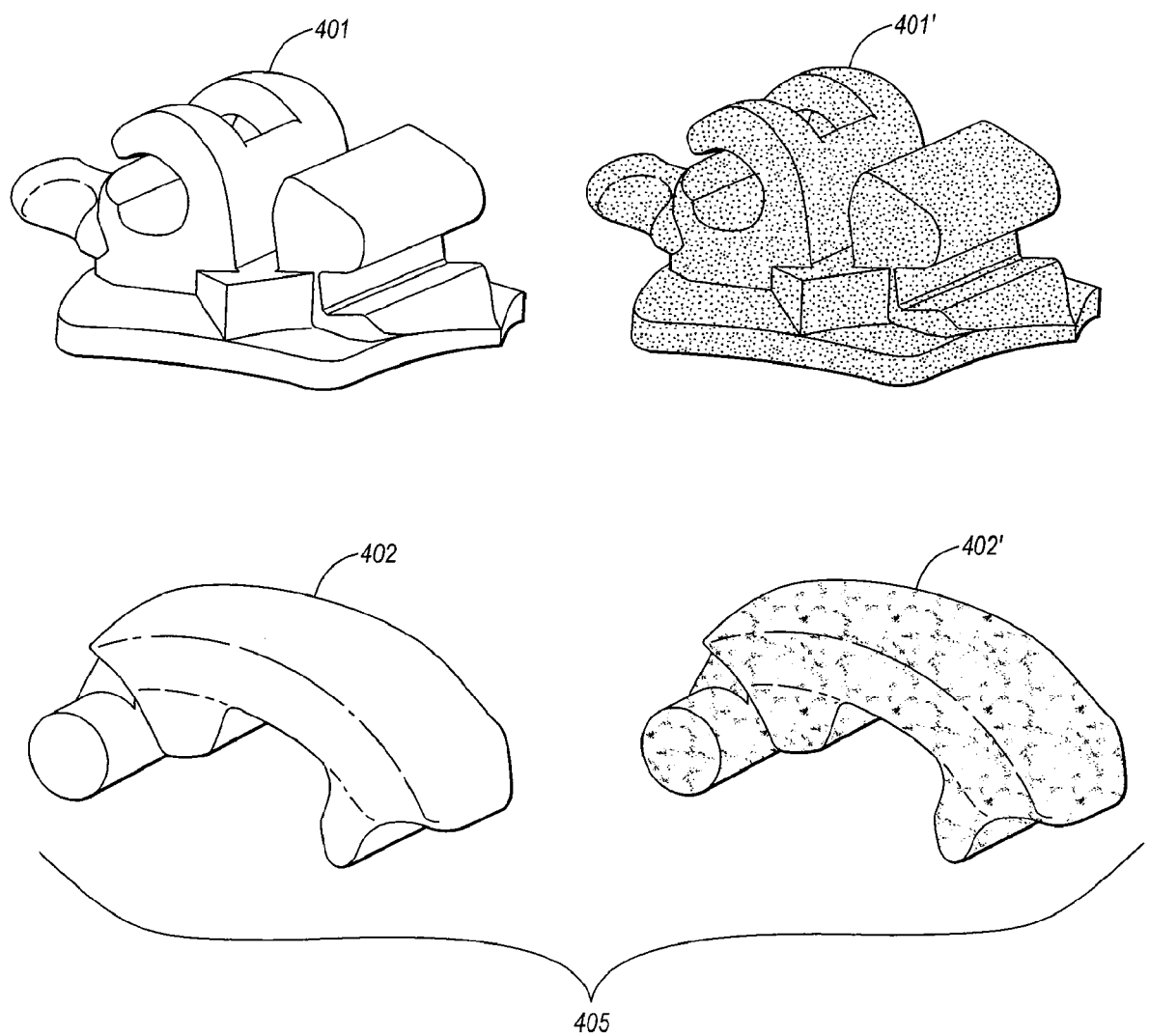
FIG. 10 is a perspective view of an exemplary kit including a plurality of bracket bases and a plurality of interchangeable ligation covers.

Referring to FIG. 10, the bracket bases and interchangeable ligation covers may be provided in a kit 405. According to one such embodiment, a kit 405 includes a plurality of bracket bases 401 and 401', and a plurality of interchangeable ligation covers 402 and 402'. Each interchangeable ligation cover (402 and 402') is attachable to any of the bracket bases (401 and 401'). At least one of the interchangeable ligation covers is of a different color and/or formed of a different material relative to at least one other interchangeable ligation cover. In order to provide even greater selection choices to the patient and the practitioner, the plurality of bracket bases may include bases formed of various different materials (e.g., ceramic, glass, metal, polymeric resin). Although illustrated with the bracket base and interchangeable ligation cover embodiments of FIGS. 1 and 2, it is to be understood that other bracket bases and interchangeable ligation covers may be used (e.g., the embodiments of FIGS. 5 and 6).

IV. Exemplary Method of Use

Figure 11A:
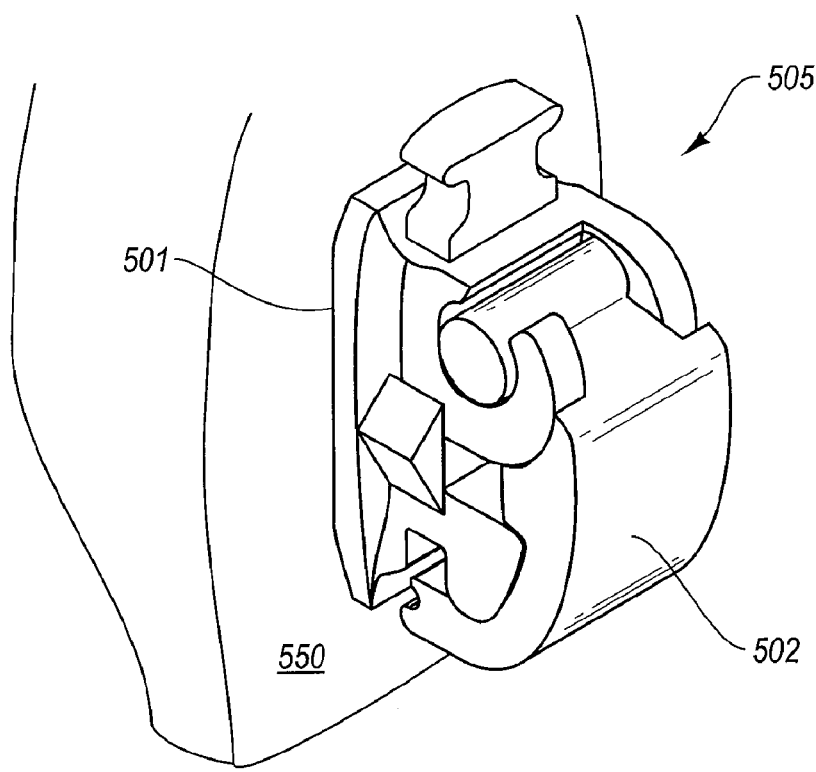
FIG. 11A is a perspective view of the orthodontic bracket that forms part of the system shown in FIG. 1 attached to the tooth of a patient.
Figure 11B:
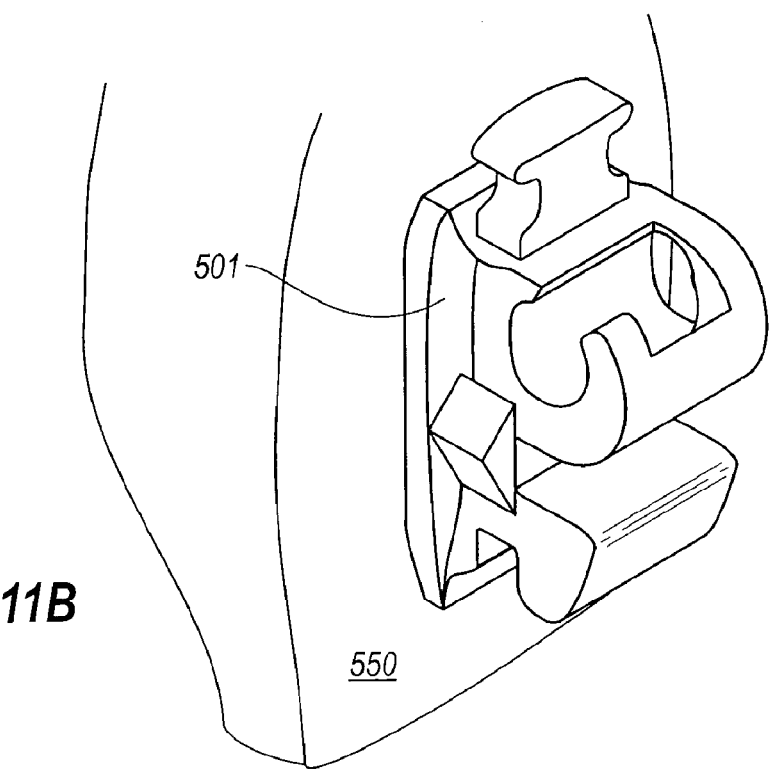
FIG. 11B is a perspective view of the orthodontic bracket base of FIG. 11A still attached to the tooth of a patient after the first interchangeable ligation cover has been removed.
Figure 11C:
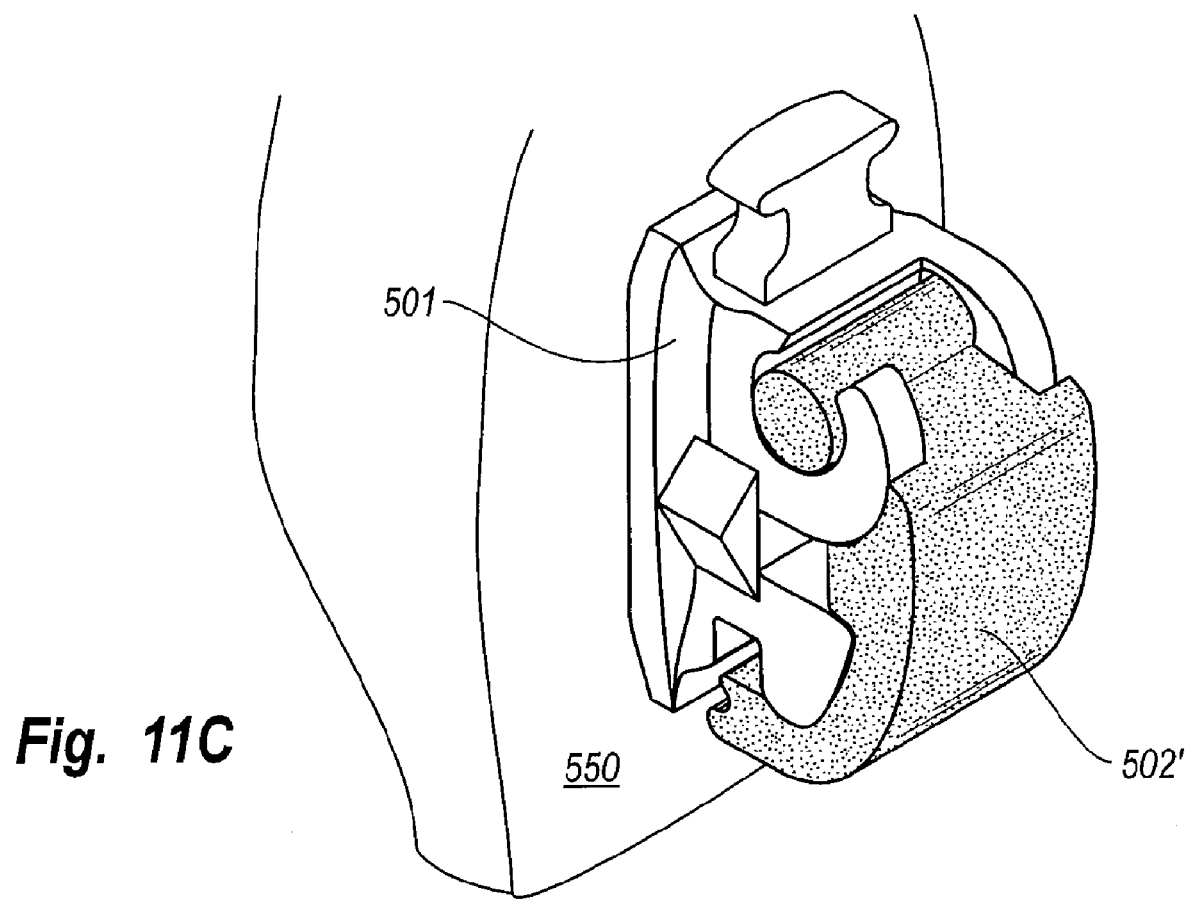
FIG. 11C is a perspective view of the orthodontic bracket base of FIG. 11B after the first interchangeable ligation cover has been replaced with a second interchangeable ligation cover.

FIGS. 11A-11C illustrate an exemplary method of using the inventive orthodontic bracket system. FIG. 11A shows an orthodontic bracket 505 including a bracket base 501 and a first interchangeable ligation cover 502 bonded to a tooth 550. FIG. 11B illustrates the tooth 550 with the bracket base 501 still bonded to the tooth after first interchangeable ligation cover 502 has been removed. FIG. 11C illustrates the tooth 550 with bracket base 501 bonded to the tooth, and a second interchangeable ligation cover 502' that has replaced first interchangeable ligation cover 502.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orthodontic bracket kit that permits selective intraoral attachment of a desired ligation cover, from among a plurality of different ligation covers, to a bracket base, the kit comprising:

a bracket base for attachment to a tooth, the bracket base including an arch wire slot formed therein adapted to receive an arch wire, the bracket base being configured so as to releasably receive one of a plurality of interchangeable ligation covers of the bracket system and so as to permit selective intraoral attachment to and removal from the bracket base of each of the plurality of different ligation covers of the bracket system as desired while the bracket base remains attached to a tooth; and at least two interchangeable ligation covers formed of different types of material selected from the group consisting of metal, glass, and polymeric resins, each being configured so as to be selectively attachable to and removable from the bracket base, a first interchangeable ligation cover releasably attachable to the bracket base and movable between an open, non-ligating position and a closed, ligating position relative to the arch wire slot, wherein the first interchangeable ligation cover is removable from the bracket base, thereby permitting removal and replacement of the first interchangeable ligation cover with another cover, the first interchangeable ligation cover being formed from a first material; and a second interchangeable ligation cover releasably attachable to the bracket base upon removal of the first interchangeable ligation cover from the bracket base and selectively movable relative to the bracket base between an open, non-ligating position and a closed, ligating position relative to the arch wire slot, the second interchangeable ligation cover being formed of a second material that is different from the first material from which the first interchangeable ligation cover is formed so that the second interchangeable ligation cover provides a different appearance than the first interchangeable ligation cover, wherein each of the first and second interchangeable ligation covers comprises a pair of inwardly oriented pins with a gap in between formed on each of the first and second interchangeable ligation covers and wherein the bracket base comprises a link guide formed on the bracket base, the link guide having a guide recess for captively retaining the inwardly oriented pins, the pins and link guide together forming a hinge such that once attached to the bracket base, the first or second interchangeable ligation cover can be selectively pivoted about the hinge relative to the bracket base between an open, non-ligating position and a closed, ligating position relative to the at least one arch wire slot.

2. An orthodontic bracket system as recited in claim 1, wherein the bracket base is formed from at least one material selected from the group consisting of ceramic, glass, metal, and a polymeric resin.

3. An orthodontic bracket system as recited in claim 2, wherein at least one of the first or second interchangeable ligation covers is made from a different material than the bracket base in order to provide a different aesthetic appearance than the bracket base.

4. An orthodontic bracket system as recited in claim 1, wherein the first interchangeable ligation cover is formed from one of glass, metal, or a polymeric resin and the second interchangeable ligation cover is formed from a different one of glass, metal, or a polymeric resin.

5. An orthodontic bracket system as recited in claim 4, wherein the first interchangeable ligation cover is formed of a polymeric resin and the second interchangeable ligation cover is formed of a metal or glass.

6. An orthodontic bracket system as recited in claim 5, wherein the first interchangeable ligation cover is formed of a glass and the second interchangeable ligation cover is formed of a polymeric resin or metal.

7. An orthodontic bracket system as recited in claim 5, wherein the first interchangeable ligation cover is formed of a metal and the second interchangeable ligation cover is formed of a glass or polymeric resin.

8. An orthodontic bracket system as recited in claim 1, wherein at least one of the first and second interchangeable ligation covers is impregnated and/or coated with a medicament.

9. An orthodontic bracket system as recited in claim 8, wherein the medicament comprises fluoride.

10. An orthodontic bracket system as recited in claim 1, wherein the first interchangeable ligation cover has a first non-tooth color that differs from a tooth to which the bracket base is to be attached, and wherein the second interchangeable ligation cover has a second non-tooth color that differs from the first non-tooth color.

11. An orthodontic bracket system as recited in claim 1, wherein the first interchangeable ligation cover is formed from a first type of metal, ceramic, or polymer, and wherein the second interchangeable ligation cover is formed from a second type of metal, ceramic, or polymer.

12. A kit of orthodontic brackets that permits selective intraoral attachment of a desired ligation cover to a selected bracket base from among a plurality of ligation covers and bracket bases, the kit comprising:

a plurality of bracket bases, each bracket base having an arch wire slot formed therein configured to receive an arch wire, each bracket base including a link guide having a guide recess for releasable attachment to one of a plurality of interchangeable ligation covers of the bracket system and so as to permit selective attachment to and intraoral removal from the bracket base of each of the plurality of different ligation covers of the bracket system while the bracket base remains attached to a tooth; and a plurality of interchangeable ligation covers, each ligation cover including a pair of inwardly oriented pins with a gap in between for releasable hinged attachment to the guide recess of one of the plurality of bracket bases, the pins and link guide together providing a hinge such that once one of the interchangeable ligation covers is attached to the one of the bracket bases the ligation cover can be selectively pivoted about the hinge relative to the bracket base between an open, non-ligating position and a closed, ligating position relative to the arch wire slot of the bracket base to which the ligation cover is attached;

wherein at least one of the plurality of interchangeable ligation covers has a different color and/or is formed of a different material relative to at least one other of the plurality of interchangeable ligation covers.

13. A kit as recited in claim 12, wherein each bracket base of the plurality of bracket bases is formed from at least one material selected from the group consisting of ceramic, glass, metal, and a polymeric resin.

14. A kit as recited in claim 13, wherein at least one of the interchangeable ligation covers is formed from a different material than at least one of the bracket bases so as to provide a different aesthetic appearance.

15. A kit as recited in claim 12, wherein each interchangeable ligation cover of the plurality of interchangeable ligation covers is formed from at least one material selected from the group consisting of glass, metal, and a polymeric resin.

16. A kit as recited in claim 15, wherein at least one of the interchangeable ligation covers is formed of a first one of glass, metal or polymer resin and at least one other of the interchangeable ligation covers is formed of a different one of glass, metal or polymeric resin.

17. A kit as recited in claim 10, wherein at least one of the interchangeable ligation covers has a first non-tooth color that differs from a color of a tooth to which any of the bracket base is to be attached, and wherein at least one other of the interchangeable ligation covers has a second non-tooth color that differs from the first non-tooth color.

18. A kit as recited in claim 10, wherein at least one of the interchangeable ligation covers is formed from a first type of metal, ceramic, or polymer, and wherein at least one other of the interchangeable ligation covers is formed from a second type of metal, ceramic, or polymer.

19. An orthodontic bracket kit that permits selective intraoral attachment of a desired ligation cover, from among a plurality of different ligation covers, to a bracket base, the kit comprising:

a bracket base for attachment to a tooth, the bracket base including an upper surface with an arch wire slot formed therein and adapted to receive an arch wire, the bracket base including a link guide having a guide recess for releasable attachment to each of a plurality of interchangeable ligation covers one at a time;

a first interchangeable ligation cover including a pair of first inwardly oriented pins with a gap in between for releasable hinged attachment to the link guide of the bracket base, the first pins and link guide forming a first hinge when the first ligation cover is attached to the bracket base so that the first ligation cover can be selectively pivoted about the hinge relative to the bracket base between an open, non-ligating position and a closed, ligating position relative to the arch wire slot wherein the first interchangeable ligation cover is removable from the bracket base while the bracket base remains attached to a tooth, thereby permitting intraoral removal and replacement of the first interchangeable ligation cover with another cover; and a second interchangeable ligation cover including a pair of second inwardly oriented pins with a gap in between for releasable attachment to the link guide of the bracket base upon removal of the first interchangeable ligation cover from the bracket base, the second pins and link guide forming a second hinge when the second ligation cover is attached to the bracket base so that the second ligation cover can be selectively pivoted about the second hinge relative to the bracket base between an open, non-ligating position and a closed, ligating position relative to the arch wire slot the second interchangeable ligation having a color and/or being made from a material that differs from the color and/or material of the first interchangeable cover.

20. An orthodontic bracket system as recited in claim 19, wherein the first interchangeable ligation cover includes at least one of a graphic, figure, decal, sticker, jewelry, or LED light.

21. An orthodontic bracket system as recited in claim 19, wherein the first interchangeable ligation cover includes at least one of a fluorescent color or a bright color that is a high contrast color.

* * * * *